US00PP31696P2

(12) United States Plant Patent
Danziger

(10) Patent No.: US PP31,696 P2
(45) Date of Patent: Apr. 21, 2020

(54) ***SUTERA* PLANT NAMED 'DCOPGULPNK'**

(50) Latin Name: *Sutera cordata*
Varietal Denomination: DCOPGULPNK

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/350,027

(22) Filed: Sep. 13, 2018

(51) Int. Cl.
*A01H 5/02* (2018.01)
*A01H 6/00* (2018.01)

(52) U.S. Cl.
USPC ..... Plt./485

(58) Field of Classification Search
USPC ..... Plt./485
CPC ... A01H 5/02; A01H 5/00; A01H 6/00; A01H 1/02
See application file for complete search history.

(56) References Cited

PUBLICATIONS

Danziger Scopia Gulliver Pink retrieved on Aug. 28, 2019, retrieved from the Internet at https://danzigeronline.com/variety/scopia-gulliver-pink-2/, 6 pp. (Year: 2019).*
Greenstreet Growers Liner 2018, retrieved on Aug. 28, 2019, retrieved from the Internet at https://www.growgreenstreet.com/wp-content/uploads/2017/10/LinerCatalog2018.pdf, 3 cover pages, pp. 1-2 (Year: 2018).*
Gro 'n Sell Elements for Your Success 2017-2018, retrieved on Aug. 28, 2019, retrieved from the Internet at http://gronsell.com/wp-content/uploads/2017/07/GNS_2018_Full_Catalog-web.pdf, 2 cover pages, pp. 1-2, 56, 58, 102-106. (Year: 2018).*
Vellekoop FloralDaily Highlights at Proven Winners, Syngenta, Danziger, Varinova, Benary, Volmary, Bailey Nurseries, 2017 retrieved Aug. 29, 2019, Internet at https://www.floraldaily.com/article/9009662/highlights-at-proven-winners-syngenta-danziger-varinova-benary-volmary-bailey-nurseries/, 9 pp. (Year: 2017).*

* cited by examiner

*Primary Examiner* — June Hwu
(74) *Attorney, Agent, or Firm* — Cassandra Bright

(57) ABSTRACT

A new and distinct *Sutera* cultivar named 'DCOPGULPNK' is disclosed, characterized by early and abundant flowering, extra-large pink flowers, medium plant vigor and a semi-trailing growth habit. The new variety is a *Sutera*, normally produced as an outdoor garden or container plant.

2 Drawing Sheets

Figure 1:
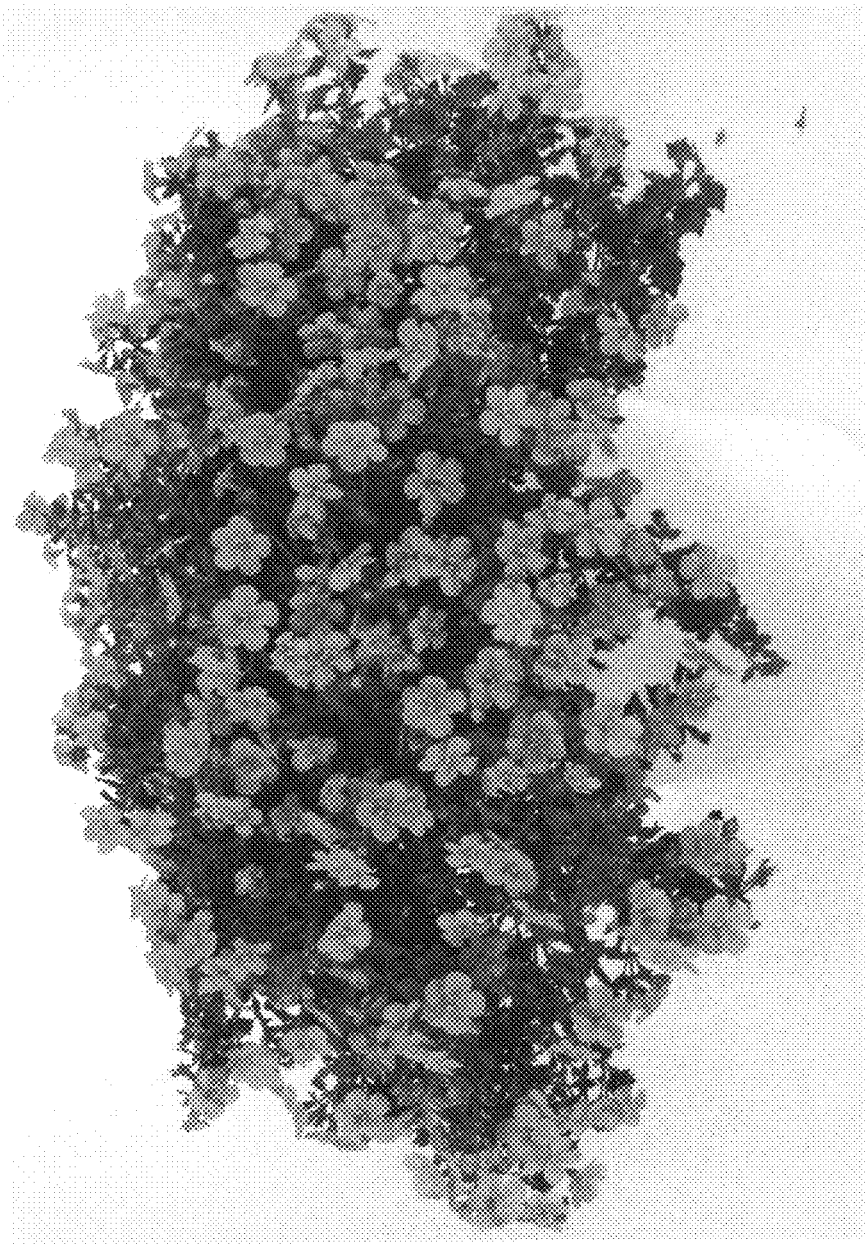

Latin name of the genus and species: *Sutera cordata*.
Variety denomination: 'DCOPGULPNK'.

BACKGROUND OF THE INVENTION

The new *Sutera* cultivar is a product of a planned breeding program conducted by the inventor, Gavriel Danziger, in Moshav Mishmar Hashiva, Israel. The objective of the breeding program was to produce new *Sutera* varieties for ornamental commercial applications. The open pollination resulting in this new variety was made during April of 2014.

The seed parent is the unpatented, proprietary variety referred to as *Sutera* 'cv. 13-2911'. The pollen parent is unknown as it was an open pollination breeding program. The new variety was discovered in January 2015 by the inventor in a group of seedlings resulting from the 2014 open pollination, in a research greenhouse in Moshav Mishmar Hashiva, Israel.

Asexual reproduction of the new cultivar was performed by terminal vegetative cuttings. This was first performed at a research greenhouse in Moshav Mishmar Hashiva, Israel in February of 2015 and has shown that the unique features of this cultivar are stable and reproduced true to type in more than 20 successive generations.

SUMMARY OF THE INVENTION

The cultivar 'DCOPGULPNK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCOPGULPNK' These characteristics in combination distinguish 'DCOPGULPNK' as a new and distinct *Sutera* cultivar:

1. Semi-trailing growth habit.
2. Extra-large, pink flowers.
3. Branched.
4. Early, abundant flowering.
5. Medium vigor.

Plants of the new cultivar 'DCOPGULPNK' are similar to plants of the seed parent, *Sutera* 'cv. 13-2911' in most horticultural characteristics, however, plants of the new cultivar 'DCOPGULPNK' differ in the following;

1. New variety has a semi-trailing growth habit; seed parent has a trailing growth habit.
2. New variety has extra-large pink flowers; seed parent has medium-sized light pink flowers.
3. New variety is very branched; seed parent is medium branched.
4. New variety has early, abundant flowering; seed parent has early, medium quantity of flowering.

5. New variety has a medium vigor; seed parent has a strong vigor.

COMMERCIAL COMPARISON

Plants of the new cultivar 'DCOPGULPNK' are comparable to the commercial variety *Sutera* 'DANCOP27', U.S. Plant Pat. No. 19,782. The two *Sutera* varieties are similar in most horticultural characteristics; however, the new variety 'DCOPGULPNK' differs in the following:

1. Comparison variety has light pink flowers with a violet center, whereas new variety has pink flowers.
2. Comparison variety is very branched whereas new variety is less branched.
3. Comparison variety has large flowers whereas new variety has extra large flowers.

Plants of the new cultivar 'DCOPGULPNK' can also be comparable to the unpatented commercial variety 'DANCOP102', U.S. Plant Pat. No. 26,521. The two *Sutera* varieties are similar in most horticultural characteristics; however, the new variety 'DCOPGULPNK' differs in the following:

1. Comparison variety has white flowers whereas new variety has pink flowers.
2. Comparison variety has longer branches and more elongated growth habit than the new variety.
3. Comparison variety has strong vigor whereas new variety has medium vigor.

BRIEF DESCRIPTION OF THE PHOTOGRAPHS

The accompanying photograph in FIG. 1 illustrates in full color a typical plant of 'DCOPGULPNK' grown in a greenhouse, in a 13 cm pot. Age of the plant photographed is approximately 3 months old from a rooted cutting.

Figure 2:
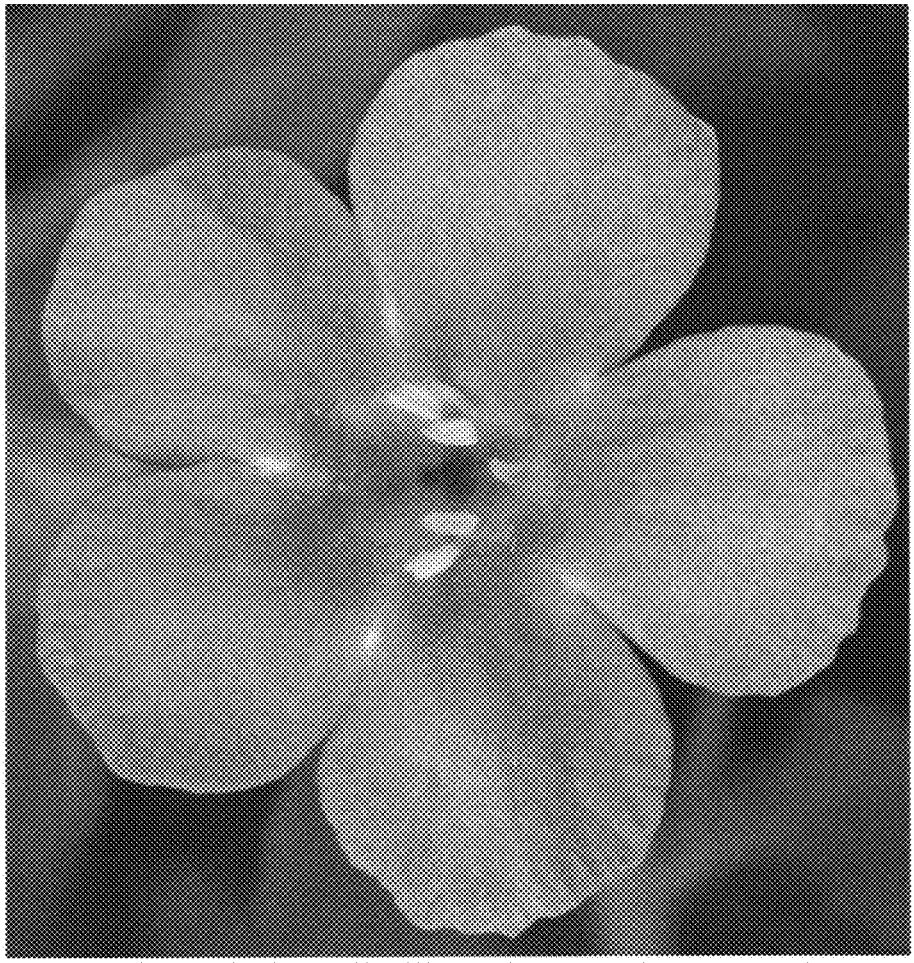

FIG. 2 illustrates a close up of a typical flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCOPGULPNK' plants grown in the Winter to Spring in moderate climate in a greenhouse, in Moshav Mishmar Hashiva, Israel. The growing temperature ranged from 15° C. to 26° C. during the day and from 13° C. to 16° C. during the night. General light conditions are normal sunlight and numerical values represent averages of typical plant types.

Botanical classification: *Sutera cordata* 'DCOPGULPNK'.

PROPAGATION

Type of propagation typically used: Terminal vegetative cuttings.

Time to initiate roots: 7 to 10 days at approximately 20° C.

Root description: Fine, fibrous roots. Light tan in color, not accurately measured with R.H.S. chart.

PLANT

Age of plant described: Approximately 3 months from rooted cutting.

Container size of the plant described: 13 cm.

Growth habit: Semi-trailing.

Height: About 12 cm.

Plant spread: About 55 cm.

Growth rate: Medium.

Branching characteristics:

Length of primary lateral branches: About 30 cm.

Diameter of lateral branches: About 0.2 cm.

Quantity of primary lateral branches: About 8.

Characteristics of primary lateral branches:

*Form*.—Cylindrical.

*Diameter*.—About 0.2 cm.

*Color*.—RHS Yellow-Green 146 A.

*Texture*.—Velvety.

*Strength*.—Good.

Internode length: About 2 cm.

FOLIAGE

Leaf:

*Arrangement*.—Opposite, petiolate.

*Quantity*.—Approximately 70 per branch.

*Average length*.—2.8 cm.

*Average width*.—2.5 cm.

*Shape of blade*.—Elliptic.

*Apex*.—Acute.

*Base*.—Acuminate.

*Margin*.—Serrate.

*Texture of top surface*.—Velvety.

*Pubescence*.—Velvety, upper and lower surfaces.

*Aspect*.—About 90° to the branch.

*Color*.—Young foliage upper side: RHS Green 137 B. Young foliage under side: RHS Green 137 C. Mature foliage upper side: RHS Yellow-Green 147 A. Mature foliage under side: RHS Yellow-Green 147 B.

*Venation*.—Type: Pinnate. Venation color upper side: RHS Yellow-Green 147 A. Venation color under side: RHS Yellow-Green 147 C.

*Petiole*.—Length: About 0.5 cm. Diameter: About 0.2 cm. Color: RHS Yellow-Green 147 A.

*Texture*.—Slightly velvety.

FLOWER

Natural flowering season: All year round.

Days to flowering from rooted cutting: About 45.

Inflorescence and flower type and habit: Axillary, solitary, salverform single flowers.

Rate of flower opening: 3 to 5 days from bud to fully opened flower.

Flower longevity on plant: About 7 days.

Persistent or self-cleaning: Persistent.

Bud:

*Shape*.—Spatulate.

*Length*.—About 1 cm.

*Diameter*.—About 0.6 cm.

*Color*.—RHS Purple 75 A.

Flower size:
*Diameter*.—About 2.7 cm.
*Length*.—About 1.5 cm.
*Corolla tube diameter*.—About 0.4 cm.
*Corolla tube length*.—About 4 mm.
Corolla/petals:
*Arrangement*.—Symmetric.
*Lobe length*.—About 1.2 cm.
*Lobe width*.—About 1.0 cm.
*Quantity*.—5.
*Texture*.—Velvety.
*Lobe apex*.—Rounded.
*Lobe shape*.—Rounded.
*Margin*.—Entire.
*Aspect*.—About 90° to the tube.
*Color*.—When opening: Upper surface: RHS Purple-Violet N 80 B. With a Purple center, RHS Purple-Violet N 80 A. Lower surface: RHS Purple 76 C. Fully opened: Upper surface: RHS Purple N 78 C. Lower surface: RHS Purple N78 D. Visible Corolla tube color: Inner surface: RHS Yellow-Orange 23 A. Outer surface: RHS Yellow 9D.
Calyx/sepals:
*Quantity per flower*.—5.
*Shape*.—Linear.
*Length*.—About 0.6 cm.
*Width*.—About 0.1 cm.
*Apex*.—Acute.
*Base*.—Fused.
*Margin*.—Entire.
*Texture*.—Slightly velvety, both surfaces.
*Color*.—Upper Surface: RHS Green 137 B. Lower Surface: RHS Green 137 B.
Peduncle: None.
Pedicel:
*Length*.—Approximately 1.1 cm.
*Diameter*.—Approximately 0.1 cm.
*Color*.—Near RHS Yellow-Green 147 B.
*Orientation*.—Slanted upward and outward.
*Pubescence*.—Slightly pubescent.
Fragrance: None.

REPRODUCTIVE ORGANS

Stamens:
*Number*.—4.
*Filament length*.—Approximately 1.2 cm.
Anthers:
*Shape*.—Cylindrical.
*Length*.—Approximately 0.2 cm.
*Color*.—RHS Yellow 11 A.
*Pollen*.—Color: RHS Yellow 13 A. Quantity: Sparse.
Pistil:
*Number*.—1.
*Length*.—About 1.1 cm.
*Style*.—Length: About 0.8 cm. Color: RHS Yellow Green-150 B.
*Stigma*.—Shape: Linear. Color: RHS Yellow Green-150 A. Ovary Color: RHS Green 143 C.

OTHER CHARACTERISTICS

Seeds and fruits: About 40 elliptic, small (1 mm long) brown seeds per one elliptic Brown capsule.
Disease/pest resistance: Neither resistance nor susceptibility to pathogens and pests common to *Sutera* have been observed.
Temperature tolerance: The new variety tolerates temperatures between 5 to 40 ° C.

What is claimed is:

1. A new and distinct cultivar of *Sutera* plant named 'DCOPGULPNK' as herein illustrated and described.

* * * * *